United States Patent
Miller et al.

(10) Patent No.: US 11,731,947 B2
(45) Date of Patent: Aug. 22, 2023

(54) DEUTERATED ANTIMICROBIAL COMPOUNDS

(71) Applicant: University of Notre Dame du Lac, South Bend, IN (US)

(72) Inventors: Marvin J. Miller, South Bend, IN (US); Viktor Krchnak, South Bend, IN (US); Rui Liu, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 98 days.

(21) Appl. No.: 17/602,401

(22) PCT Filed: Apr. 3, 2020

(86) PCT No.: PCT/US2020/026618
§ 371 (c)(1),
(2) Date: Oct. 8, 2021

(87) PCT Pub. No.: WO2020/210125
PCT Pub. Date: Oct. 15, 2020

(65) Prior Publication Data
US 2022/0204463 A1    Jun. 30, 2022

Related U.S. Application Data

(60) Provisional application No. 62/832,010, filed on Apr. 10, 2019.

(51) Int. Cl.
*C07D 279/08* (2006.01)
*C07D 491/113* (2006.01)

(52) U.S. Cl.
CPC ........ *C07D 279/08* (2013.01); *C07D 491/113* (2013.01)

(58) Field of Classification Search
None
See application file for complete search history.

(56) References Cited

U.S. PATENT DOCUMENTS

| | | |
|---|---|---|
| 6,221,335 B1 | 4/2001 | Foster |
| 9,249,149 B2 | 2/2016 | Silverman et al. |
| 9,328,113 B2 | 5/2016 | Tung et al. |
| 2007/0276042 A1 | 11/2007 | Gant et al. |

FOREIGN PATENT DOCUMENTS

WO    2018055048 A1    3/2018

OTHER PUBLICATIONS

Errede et al., The Anomalous Behavior of m-Trifluoromethylnitrosobenzene Dimer, J. Org. Chem., (28);1430-1431, May 1963.

Hagen et al., "Solution and Gas Phase Deuterium Derivatization Reactions for Gas Chromatography/Microwave Emission Detection," Spectrochimica Acta Part B: Atomic Spectroscopy, 42(1-2):253-267, Dec. 1987.

Harbeson et al., "Deuterium Medicinal Chemistry: a New Approach to Drug Discovery and Development," Medchem. News,(2):8-22, May 2014.

International Search Report and Written Opinion of the ISA/US in PCT/US2020/026618, dated Aug. 14, 2020; 10pgs.

Kloss et al., "In Vivo Dearomatization of the Potent Antituberculosis Agent BTZ043 via Meisenheimer Complex Formation," Angew Chem Int Ed Engl., 56(8):2187-2191, Feb. 2017.

Makarov et al. "Towards a New Combination Therapy for Tuberculosis with Next Generation Benzothiazinones," EMBO Mol Med., 6(3):372-383, Mar. 2014.

Peabody et al., "Synthesis of Selectively Deuterated Fulvenes and Indenes From Enediynes," Org Biomol Chem., Jan. 3, 2005 (2):216-221.

Richter et al., "Novel Insight Into the Reaction of Nitro, Nitroso and Hydroxylamino Benzothiazinones and of Benzoxacinones With Mycobacterium Tuberculosis DprE1," Sci Rep., 8:13473, Sep. 2018.

Spaggiari et al., "Development and Validation of a Multiplex UHPLC-MS/MS Method for the Determination of the Investigational Antibiotic Against Multi-Resistant Tuberculosis Macozinone (PBTZ169) and Five Active Metabolites in Human Plasma," PLoS One, 14(5):e0217139, May 2019.

Suwinski et al., "Reduction of Aromatic Nitrocompounds by Sodium Borohydride in Methanol in the Presence of Sodium Methoxide," Tetrahedron, 52(28):9541-9552, Jul. 1996.

Tiwari e tal., "Thiolates Chemically Induce Redox Activation of BTZ043 and Related Potent Nitroaromatic Anti-Tuberculosis Agents," J. Am. Chem. Soc., 135(9):3539-3549, Feb. 2013.

*Primary Examiner* — Samantha L Shterengarts

(74) *Attorney, Agent, or Firm* — Haukaas Fortius PLLC; Michael Haukaas

(57) ABSTRACT

Substituted nitrobenzothiazinones (BTZs) are potent antituberculosis prodrugs that are reductively activated to produce nitroso moieties that form covalent adducts with a cysteine residue of decaprenylphosphoryl-β-D-ribose-2'-oxi-dase (DprE1) of *Mycobacterium tuberculosis* (Mtb). The resulting cell wall synthesis inhibition is lethal to Mtb, leading to consideration of development of BTZs for clinical use. The hydride-induced reduction of the nitroaromatic proceeds by reversible formation of the corresponding Meisenheimer complex. Herein we demonstrate that chemical reduction of BTZ043 with NaBD4 followed by reoxidation incorporates deuterium into the core nitro aromatic warhead. Subsequent reduction of the deuterated species is not affected, but, as expected, reoxidation is slowed by the deuterium isotope effect, thus prolonging the lifetime of the active nitroso oxidation state.

20 Claims, 1 Drawing Sheet

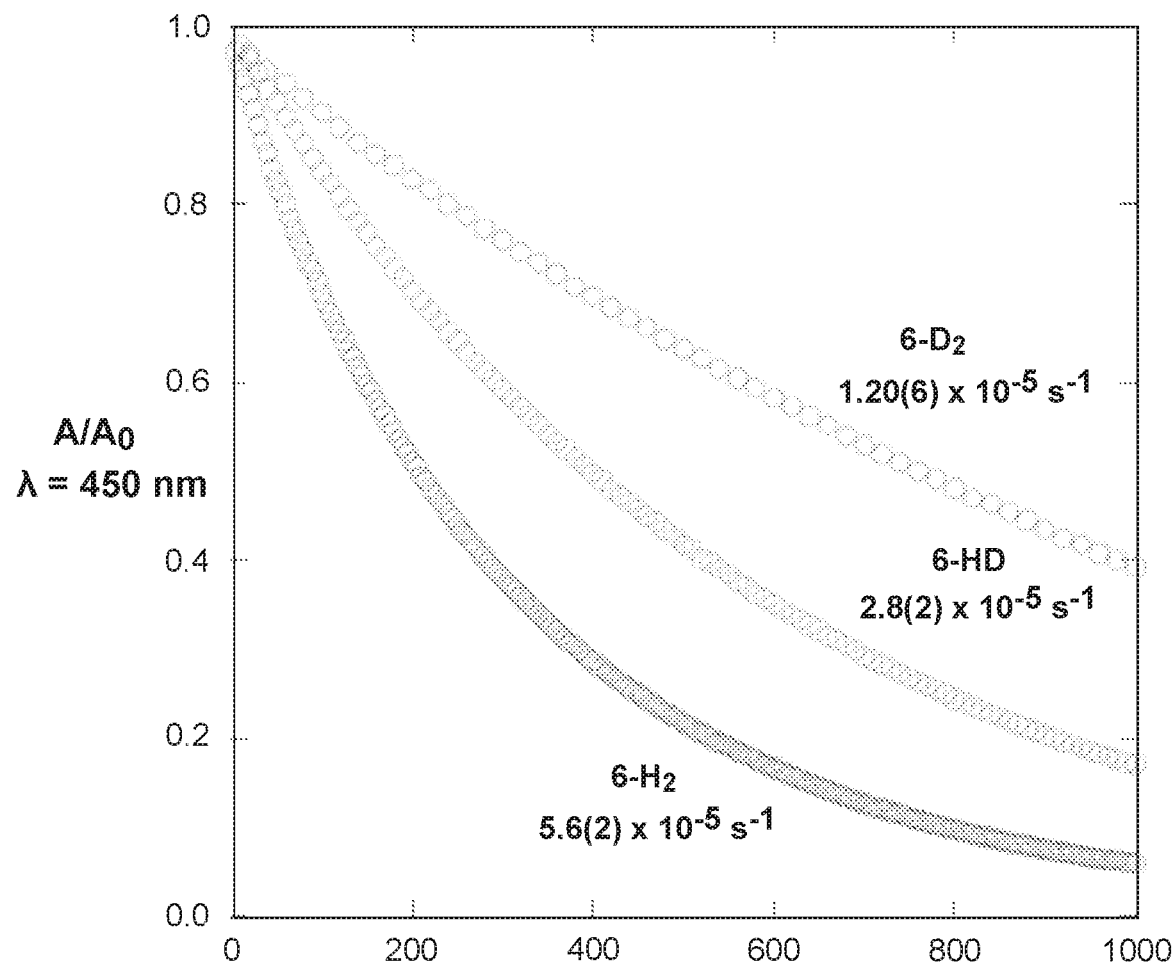

DEUTERATED ANTIMICROBIAL COMPOUNDS

RELATED APPLICATIONS

This application is a National Stage filing under 35 U.S.C. § 371 of International Application No. PCT/US2020/026618 filed Apr. 3, 2020, which claims priority under 35 U.S.C. § 119(e) to U.S. Provisional Patent Application No. 62/832,010 filed Apr. 10, 2019, which applications are incorporated herein by reference.

GOVERNMENT SUPPORT

This invention was made with government support under grant AI054193 awarded by the National Institutes of Health. The government has certain rights in the invention.

BACKGROUND OF THE INVENTION

Replacement of carbon-hydrogen bonds with isotopic carbon-deuterium bonds results in a kinetic isotope effect that is reflected in a change in the rate of chemical reactions involving those bonds. Studies of isotope effects are useful for testing proposed reaction mechanisms including enzymatic and metabolic processes in biological systems. Also, deuterium incorporation can sometimes significantly alter the metabolic profile of a molecule, thereby resulting in changes in the ratio of parent drug to metabolites and changes in the amounts of metabolites formed. Thus, substitutions of metabolically labile C—H bonds for stronger C-D bonds can improve pharmacodynamics, tolerability, and efficacy of a therapeutic agent. While several deuterated analogs of drugs have been described and found to have improved properties relative to their C—H analogs, syntheses of specifically deuterated compounds often involve extensive modifications of the synthetic procedures used to obtain the parent drugs.

Tuberculosis (TB) now ranks above HIV/AIDS as the leading cause of death from a single infectious agent and is the ninth leading cause of death worldwide. Approximately two billion people are currently infected with *Mycobacterium tuberculosis* (Mtb), the bacterium that causes TB. While most infections are latent, people with weakened immune systems are exceptionally prone to develop active cases.

SUMMARY

These results are consistent with the hydride-generated Meisenheimer complexes being key intermediates to the nitroso moieties that are responsible for DprE1 inactivation. Thus, we were interested in determining if replacement of the ortho and para hydrogens with deuterium in the electrophilic nitro-substituted "warhead" core could extend the lifetime of these important Meisenheimer complexes by deuterium isotope effect slowing the reoxidation process.

Accordingly, this disclosure provides a compound of Formula IA, IB, or IC:

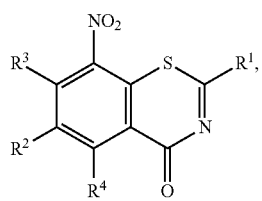
(IA)

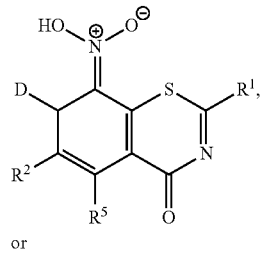
(IB)

or

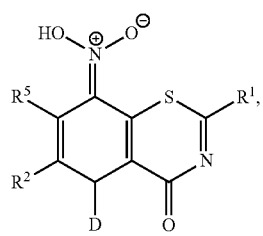
(IC)

or an azoxy dimer or salt thereof;
wherein
$R^1$ is 2-($C_1$-$C_6$)alkyl-1,4-dioxa-8-azaspiro[4.5]decan-8-yl or 4-(($C_3$-$C_6$)cycloalkyl methyl)piperazin-1-yl;
$R^2$ is halo, cyano, —($C_1$-$C_3$)alkyl, or —O($C_1$-$C_3$)alkyl, wherein —($C_1$-$C_3$)alkyl or —O($C_1$-$C_3$)alkyl has 2 to 7 halo substituents;
$R^3$ and $R^4$ are independently H, D, halo, hydroxyl, cyano, —($C_1$-$C_6$)alkyl, wherein at least one of $R^3$ or $R^4$ is D; and
$R^5$ is H, D, halo, hydroxyl, cyano, —($C_1$-$C_6$)alkyl.

This disclosure also provides a method for treating a microbial infection comprising administering a therapeutically effective amount to a subject in need thereof a compound above of Formula IA, IB, or IC, thereby killing or inhibiting the growth of at least a portion of a plurality of microorganisms in the subject.

Additionally, this disclosure provides a method for forming a deuterated compound of Formula IA, IB, or IC, comprising:
  a) reacting or contacting a deuteride reducing agent and a compound of Formula IA wherein $R^3$ and $R^4$ are H to form a reduced intermediate; and
  b) reacting or contacting the reduced intermediate and an oxidizing agent to form a compound of Formula IA wherein at least one of $R^3$ or $R^4$ is D; or
  c) reacting or contacting the reduced intermediate and a protic reagent to form a compound of Formula IB or IC;
wherein the deuterated compound of Formula IA, IB, or IC is thereby formed.

The invention provides novel compounds of Formulas IA, IB, IC, IIA, IIB, or IIC, intermediates for the synthesis of compounds of Formulas IA, IB, IC, IIA, IIB, or IIC, as well as methods of preparing compounds of Formulas IA, IB, IC, IIA, IIB, or IIC. The invention also provides compounds of Formulas IA, IB, IC, IIA, IIB, or IIC that are useful as intermediates for the synthesis of other useful compounds. The invention provides for the use of compounds of Formulas IA, IB, IC, IIA, IIB, or IIC for the manufacture of medicaments useful for the treatment of microbial infections in a mammal, such as a human.

The invention provides for the use of the compositions described herein for use in medical therapy. The medical therapy can be treating a bacterial infection, for example, in a subject suffering from tuberculosis or leprosy. The invention also provides for the use of a composition as described herein for the manufacture of a medicament to treat an infection in a mammal, for example, tuberculosis, some forms of non-tuberculosis mycobacterial infections with the DprE1 enzyme that has an essential cysteine residue, or leprosy in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1. Reactions of isotopomers of 6 monitored at 450 nm ($CH_3OH$, 36° C.).

DETAILED DESCRIPTION

The invention provides a series of nitro benzothiazinone and nitrobenzamide compounds in which carbon hydrogen bonds have been replaced with isotopic carbon-deuterium bonds, syntheses thereof, compositions thereof, and methods of using such compounds and compositions. Various embodiments provide methods of killing and/or inhibiting the growth of *Mycobacterium tuberculosis* and methods of treating, preventing, and/or ameliorating *Mycobacterium tuberculosis* or other mycobacterial infections in a subject.

Herein, we describe facile incorporation of deuterium into the core, electrophilic warhead of the nitrobenzothiazinone BTZ043 (2), a potent antituberculosis prodrug, and its consequent influence on the enzymatically active nitroso oxidation state.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. Contacting chemicals and reagents can react together to form chemical bonds under reaction conditions disclosed herein.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease, infection, or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, N.Y., 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example., 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent, described above. The alkyl can also be optionally partially or fully unsaturated. As such, the recitation of an alkyl group can include an alkenyl or an alkynyl group. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

As is generally known, and as used herein, the term, "deuterated" means the replacement of one or more carbon-hydrogen bonds with one or more isotopic carbondeuterium bond. For example, "deuterated alkyl" means an alkyl in which at least one or more carbon hydrogen bonds are replaced with isotopic carbon-deuterium bonds.

The term "deuterated alkoxy" means an alkoxy in which at least one or more carbon hydrogen bonds are replaced with isotopic carbon-deuterium bonds. The term "deuterated cycloalkyl" means a cycloalkyl in which at least one or more carbon hydrogen bonds are replaced with isotopic carbon-deuterium bonds. The term "deuterated amine" means an amine in which at least one or more carbon hydrogen bonds are replaced with isotopic carbon-deuterium bonds. The term "deuterated alkyl amino" means an alkyl amino in which at least one or more carbon hydrogen bonds are replaced with isotopic carbon-deuterium bonds. The term "deuterated aryloxy" means an aryloxy in which at least one or more carbon hydrogen bonds are replaced with isotopic carbon-deuterium bonds. The term "deuterated heteroaryl" means a heteroaryl in which at least one or more carbon hydrogen bonds are replaced with isotopic carbon-deuterium bonds.

The term "azoxy dimer" refers to an azoxyarene, such as compound 9 in Scheme 2, that was formed from the dimerization of a nitrosoarene, such as compound 4 in Scheme 1b.

For example, an azoxy dimer of a nitroso compound disclosed herein is the product of two nitroso compounds covalently bonded together via a N=N bond formed from the nitrogen atoms of the nitroso moieties derived from the nitro compounds.

The term "microorganism or microbe" refers to a microscopic organism such as bacteria. Examples of bacteria disclosed herein are, but not limited to, *Mycobacterium*

*tuberculosis*, a species of pathogenic bacteria in the family Mycobacteriaceae and the causative agent of tuberculosis that infects lungs; and *Mycobacterium leprae* which is a bacterium that causes leprosy, a chronic infectious disease that damages the peripheral nerves and targets the skin, eyes, nose, and muscles.

Embodiments of the Invention

This disclosure provides a method for forming a deuterated compound of Formula IA, B, or IC:

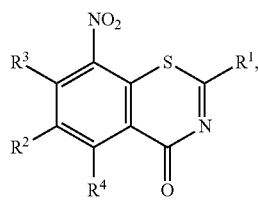
(IA)

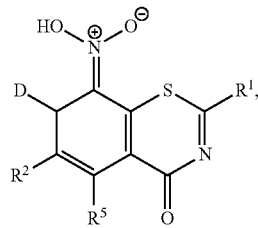
(IB)

or

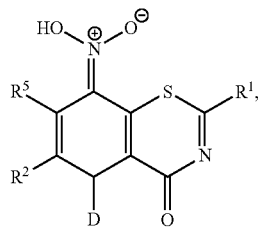
(IC)

or an azoxy dimer or salt thereof;
wherein
  $R^1$ is 2-($C_1$-$C_6$)alkyl-1,4-dioxa-8-azaspiro[4.5]decan-8-yl or 4-(($C_3$-$C_6$)cycloalkyl methyl)piperazin-1-yl;
  $R^2$ is halo, cyano, —($C_1$-$C_3$)alkyl, or —O($C_1$-$C_3$)alkyl, wherein —($C_1$-$C_3$)alkyl or —O($C_1$-$C_3$)alkyl has one or more, for example, 1 to 12 or 2 to 7 halo substituents;
  $R^3$ and $R^4$ are independently H, D, halo, hydroxyl, cyano, —($C_1$-$C_6$)alkyl; and
  $R^5$ is H, D, halo, hydroxyl, cyano, —($C_1$-$C_6$)alkyl; comprising:
a) reacting a deuteride reducing agent and a compound of Formula IA wherein $R^3$ and $R^4$ are H to form a reduced intermediate; and
b) reacting the reduced intermediate and an oxidizing agent to form a compound of Formula IA wherein at least one of $R^3$ or $R^4$ is D; or
c) reacting the reduced intermediate and a protic reagent to form a compound of Formula IB or IC;
wherein the deuterated compound of Formula IA, IB, or IC is thereby formed.

In this disclosure, method steps using the term "reacting" may be replaced with the term "contacting". In some embodiments, the method further comprises repeating steps a) and b) to increase deuterium incorporation in a compound of Formula IA; or in other embodiments repeating steps a) and c) to increase deuterium incorporation in a compound of Formula IB or IC.

In some embodiments, the reducing agent is a metal borodeuteride. In other embodiments, the oxidizing agent is a diialkylazodicarboxylate. In yet other embodiments, the protic agent is an organic acid. In other embodiments, the organic acid is acetic acid.

In various embodiments, $R^1$ is 2-methyl-1,4-dioxa-8-azaspiro[4.5]decan-8-yl and $R^2$ is $CF_3$; or in other various embodiments, $R^1$ is 4-(cyclohexylmethyl)piperazin-1-yl. In additional embodiments, $R^2$ is $CF_3$.

Also, this disclosure provides a method for treating a microbial infection comprising administering a therapeutically effective amount to a subject in need thereof a compound of Formula IA, IB, or IC:

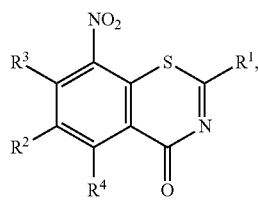
(IA)

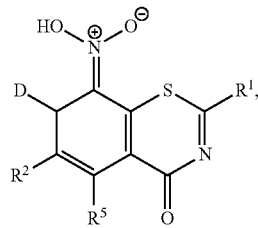
(IB)

or

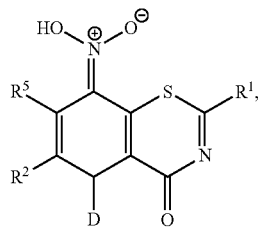
(IC)

or an azoxy dimer or pharmaceutically acceptable salt thereof;
wherein
  $R^1$ is 2-($C_1$-$C_6$)alkyl-1,4-dioxa-8-azaspiro[4.5]decan-8-yl or 4-(($C_3$-$C_6$)cycloalkyl methyl)piperazin-1-yl;
  $R^2$ is halo, cyano, —($C_1$-$C_3$)alkyl, or —O($C_1$-$C_3$)alkyl, wherein —($C_1$-$C_3$)alkyl or —O($C_1$-$C_3$)alkyl has 2 to 7 halo substituents;
  $R^3$ and $R^4$ are independently H, D, halo, hydroxyl, cyano, —($C_1$-$C_6$)alkyl, wherein at least one of $R^3$ or $R^4$ is D; and
  $R^5$ is H, D, halo, hydroxyl, cyano, —($C_1$-$C_6$)alkyl;
thereby killing or inhibiting the growth of at least a portion of a plurality of microorganisms in the subject.

In various additional embodiments, $R^1$ is 2-methyl-1,4-dioxa-8-azaspiro[4.5]decan-8-yl; or in other various embodiments, R' is 4-(cyclohexylmethyl)piperazin-1-yl. In further embodiments, $R^2$ is $CF_3$, $R^3$ is D, and $R^4$ is H. In other embodiments, $R^2$ is $CF_3$, $R^3$ is H, and $R^4$ is D. In additional embodiments, $R^2$ is $CF_3$, and $R^3$ and $R^4$ are D. In yet other embodiments, $R^2$ is $CF_3$ and $R^5$ is H or D. In other embodiments, the compound is a specific compound shown in this disclosure.

In additional embodiments, the microbial infection is a mycobacterial infection. In other embodiments, the mycobacterial infection is tuberculosis or leprosy.

This disclosure also provides a compound of Formula IA, IB, or IC:

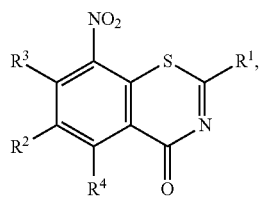
(IA)

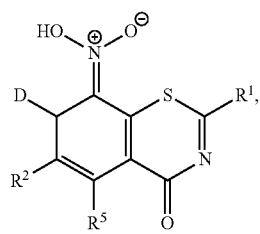
(IB)

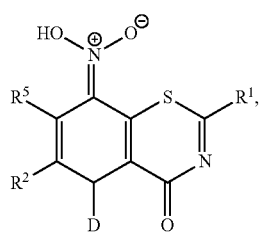
(IC)

or an azoxy dimer or salt thereof;
wherein
$R^1$ is 2-($C_1$-$C_6$)alkyl-1,4-dioxa-8-azaspiro[4.5]decan-8-yl or 4-(($C_3$-$C_6$)cycloalkyl methyl)piperazin-1-yl;
$R^2$ is halo, cyano, —($C_1$-$C_3$)alkyl, or —O($C_1$-$C_3$)alkyl, wherein —($C_1$-$C_3$)alkyl or —O($C_1$-$C_3$)alkyl has 2 to 7 halo substituents;
$R^3$ and $R^4$ are independently H, D, halo, hydroxyl, cyano, —($C_1$-$C_6$)alkyl, wherein at least one of $R^3$ or $R^4$ is D; and
$R^5$ is H, D, halo, hydroxyl, cyano, —($C_1$-$C_6$)alkyl.

Furthermore, this disclosure provides a compound of Formula IIA, JIB, or IIC:

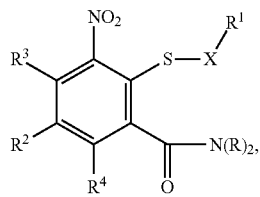
(IIA)

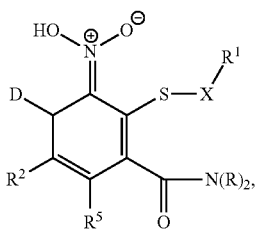
(IIB)

or

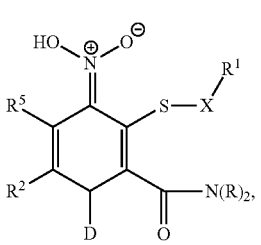
(IIC)

or an azoxy dimer or salt thereof;
wherein
the definitions of $R^1$, $R^2$, $R^3$, $R^4$, and $R^5$ are the same as described above;
R is radical or H; and
X is carbon diradical or C(=S);
wherein R and X taken together form a heterocyclic ring-double-bond when R is radical and X is carbon diradical.

In various other embodiments, $R^1$ is 2-methyl-1,4-dioxa-8-azaspiro[4.5]decan-8-yl; or $R^1$ is 4-(cyclohexylmethyl)piperazin-1-yl. In yet other embodiments, $R^2$ is $CF_3$, $R^3$ is D, and $R^4$ is H. In further embodiments, $R^2$ is $CF_3$, $R^3$ is H, and $R^4$ is D. In some other embodiments, $R^2$ is $CF_3$, and $R^3$ and $R^4$ are D. In other embodiments, $R^2$ is $CF_3$ and $R^5$ is H or D.

In various embodiments of this disclosure, the compound is:

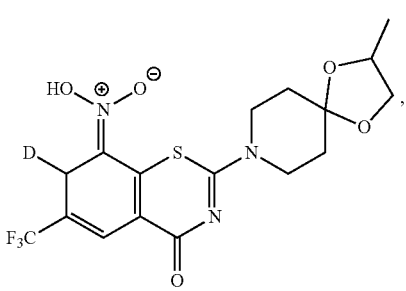

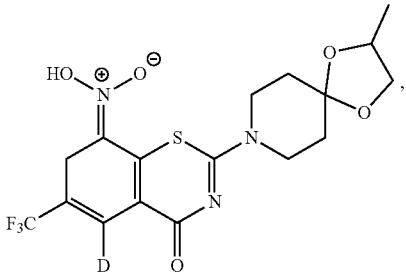

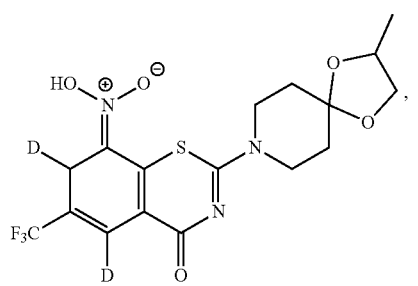
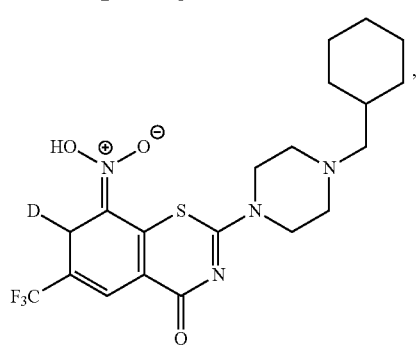
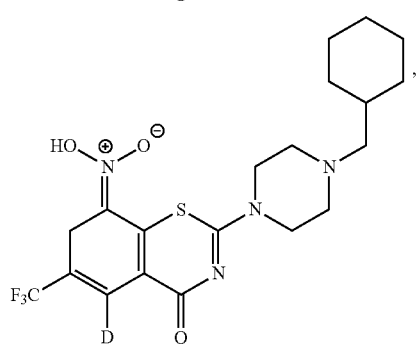
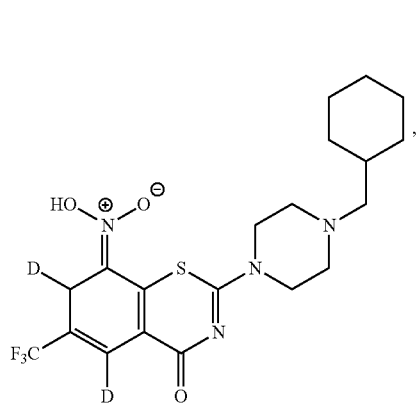
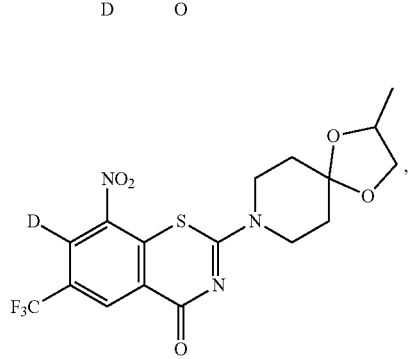
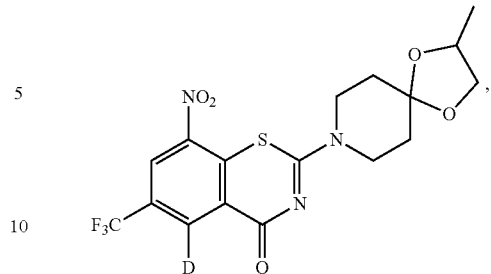
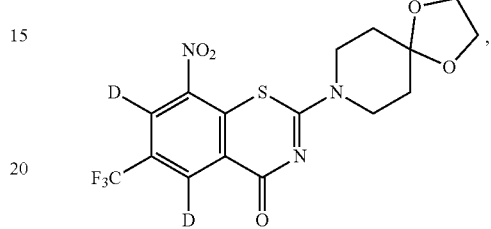
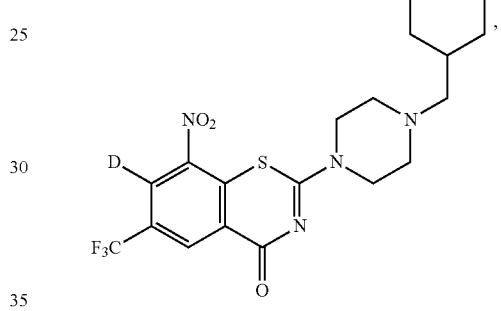
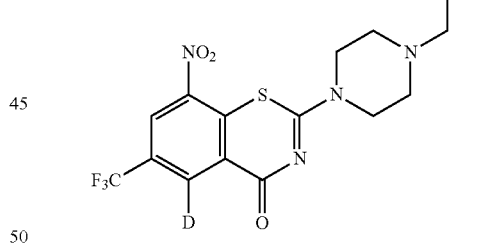
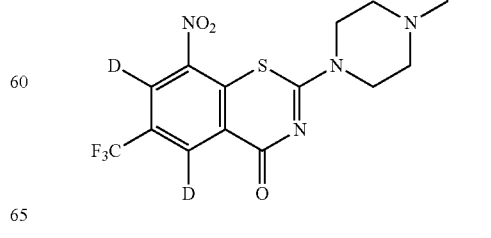
the azoxy dimer thereof.

In preferred embodiments of this disclosure, the compound is:

deuterated BTZ-043 deuterated pBTZ
(R = cyclohexylmethyl)

This disclosure also provides various embodiments of a pharmaceutical composition comprising one or more compounds disclosed herein and a pharmaceutically acceptable excipient. In some embodiments, the composition comprises one of the compounds disclosed herein, two of said compounds, or three of said compounds.

Some aspects of the invention include compounds with the following formulas A and B:

A

B or the corresponding Meisenheimer complexes $A_1$, $A_2$, $B_1$, $B_2$ and $B_3$ shown below:

$A_1$ $A_2$ $B_1$ $B_2$ $B_3$ wherein at least one of $R^2$ or $R^4$ is D;
$R^1$=NO$_2$
$R^2$=D (or H, alkyl, halo when $R^4$=D);
$R^3$=NO$_2$, CF$_3$, SO$_2$R, CN, N$_3$, halo, SF$_5$, SF$_3$, —P(O)(R)$_2$, COR, CO$_2$R, CONHR, CONRR';
$R^4$=D (or H, alkyl, halo when $R^2$=D);
$R^5$=2-methyl-1,4-dioxa-8-azaspiro[4.5]decan-8-yl or a 4-(cyclohexylmethyl)piperazin-1-yl group or is independently H, D, alkyl, deuterated alkyl, alkoxy, deuterated alkoxy, amino, alkyl amino, deuterated alkyl amino, cycloalkyl, deuterated cycloalkyl, heterocycle, deuterated heterocycle, substituted heterocycle, aryl, deuterated aryl, aryloxy, deuterated aryloxy, heteroaryl, deuterated heteroaryl, substituted heteroaryl, deuterated substituted heteroaryl;

$R^6$=2-methyl-1,4-dioxa-8-azaspiro[4.5]decan-8-yl or a 4-(cyclohexylmethyl)piperazin-1-yl group or is independently H, D, alkyl, deuterated alkyl, alkoxy, deuterated alkoxy, amino, alkyl amino, deuterated alkyl amino, cycloalkyl, deuterated cycloalkyl, heterocycle, deuterated heterocycle, substituted heterocycle, aryl, deuterated aryl, aryloxy, deuterated aryloxy, heteroaryl, deuterated heteroaryl, substituted heteroaryl, deuterated substituted heteroaryl;

$R^7$=H, D, alkyl, halo, $NO_2$, $CF_3$, $SO_2R$, CN, $N_3$, acyl;

each R and R' is independently H or —$(C_1-C_6)$alkyl;

X=S, O, NH, NR; and

Y=S, O, NH, NR.

In another aspect, the invention also provides for a method of treating a tuberculosis mycobacterial infection or non-tuberculosis mycobacterial infection in a subject, which includes administering to said subject any one or more of the compounds or compositions described herein.

In another aspect, the invention also provides for a method of killing or inhibiting the growth of *M. tuberculosis, M. avium, M. leprae,* or *M. ulcerans,* or a combination thereof, in a subject, comprising administering to said subject any one or more of the compounds or compositions described herein.

In another aspect, the invention also provides for any one or more of the compounds or compositions described herein for treatment of a tuberculosis mycobacterial infection or nontuberculosis mycobacterial infection.

In various embodiments, the compounds or methods herein are represented by compounds of Formula IA, IB, IC, IIA, IIB, IIC, A, B, $A_1$, $A_2$, $B_1$, $B_2$, $B_3$, or one or more of any specifically disclosed compound provided by this disclosure.

Results and Discussion

In 2012, bedaquiline (TMC207), the first new anti-TB agent after a multidecade drought, was approved for use in treatment of MDR-TB. It is a diarylquinoline that inhibits mycobacterial adenosine triphosphate (ATP) synthase. This approval stimulated further interest in discovery and development as well as clinical evaluation of potential new therapies for treatment of TB. The combined efforts of academic, institutional, government, industrial groups, and regulators have enhanced the pipeline related to new anti-TB agents, yet extensive efforts are still needed. The recent shift from target-based approaches to those based on phenotypic screens has accelerated discovery and development of new anti-TB lead compounds. Among the most potent classes of investigational anti-TB agents are the nitro-substituted benzothiazinones, represented by BTZ043 (2; Scheme 1a), which recently successfully finished Phase I clinical trials. The related pBTZ169 (3; Scheme 1a) is in Phase II trials in Russia. The first reported nitro-substituted benzothiazinone, BTZ043, was discovered during studies of nitroaryl dithiocarbamates (DTCs, 1) that had moderate anti-TB activity but, during cultivation of mycobacteria in the presence of DTCs, cyclized to the benzothiazinones that have low nanomolar anti-Mtb activity in whole cell assays.

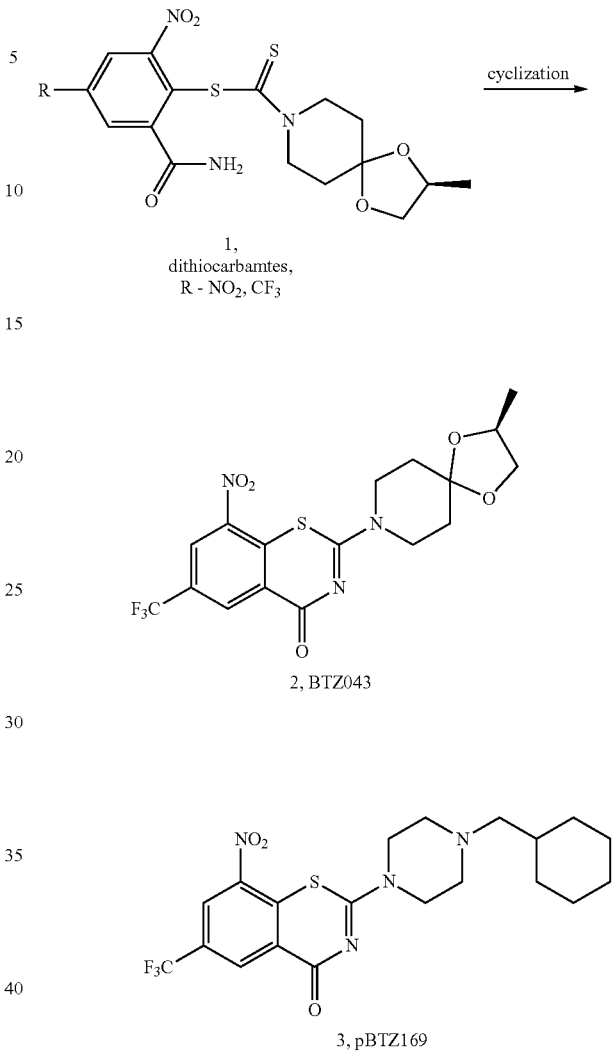

Scheme 1a. Discovery of BTZ043 and structure of pBTZ169.

The nitrobenzothiazinone (BTZ) compounds act as prodrugs, which, upon activation by reduction of the nitro substituent to an electrophilic nitroso moiety, 4, induce suicide inhibition of the enzyme decaprenylphosphoryl-β-$_D$-ribose-2'-oxidase (DprE1) of Mtb. DprE1 mediates biosynthesis of decaprenylphosphoryl-β-$_D$-arabinose (DPA), which is needed for assembly of the complex cell wall of mycobacteria. Previous studies revealed formation of a "semimercaptal adduct" (5) at the active site of DprE1 from reaction of the active-site cysteine with the nitroso intermediate (4) derived from BTZ043. Resistant mutants and other forms of mycobacteria that are less susceptible to the benzothiazinones contain active site alanine or serine instead of the active site cysteine. Separate reduction of the nitro group to the corresponding hydroxylamine and amine are also detrimental to anti-TB activity. While the mechanistic details related to the reduction of the nitro group of BTZ043 to the nitroso intermediate are yet to be fully elucidated, the DprE1-mediated process does require biological reductants (Scheme 1b). The ultimate result is that the nitrobenzothiazinones have low nanomolar activity against mycobacteria, including Mtb, that have the essential cysteine-containing DprE1 enzyme.

Scheme 1b. Formation of a Nitroso Moiety from BTZ043 and Reaction with the Target DprE1 Enzyme.

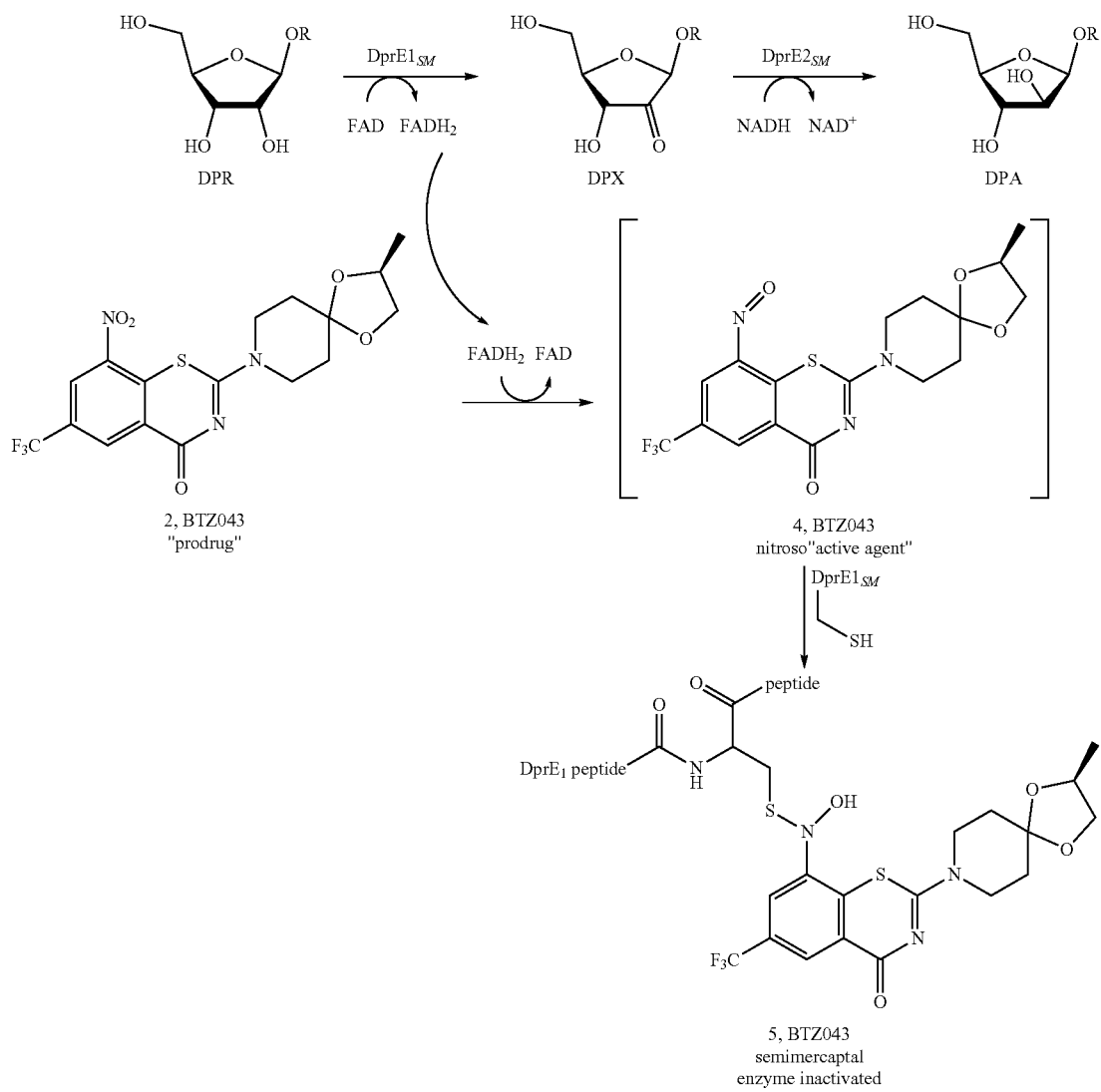

We previously reported that thiolates and other nucleophiles, including hydride, react directly and cleanly with BTZ and related nitroaromatic compounds through addition ortho and/or para to the essential nitro group with concomitant reduction of the nitro group. The initial products from chemical hydride reduction are orange/red dearomatized Meisenheimer complexes (6a and 6b) that can be isolated and fully characterized. Interestingly, metabolically only the Meisenheimer complex (6b) corresponding to the para attack of hydride is formed. Dehydration and rearomatization of the Meisenheimer complexes can provide the enzymatically reactive nitroso moiety, 4 (Scheme 1b).

As indicated in Scheme 2, the hydride reduction is reversible. Thus, while Meisenheimer complexes 6a and 6b can be isolated and stored as solids under inert atmosphere, solutions of the mixture exposed to air slowly (overnight at room temperature) oxidize to regenerate the starting BTZ043 (2) cleanly. Interestingly, in argon sparged solvents, the Meisenheimer complexes also react, but LC/MS of the reaction mixture not only shows regenerated BTZ043 (2) but also significant amounts of the corresponding amine (7), hydroxylamine (8), and azoxyarene (9). It is well-known that hydride reduction of aromatic nitro groups can generate azoxyarenes that form from the corresponding nitroso intermediates, which would correspond to nitrosoarene 4 in this case. We also have previously demonstrated that nitrosoarene 4 and the corresponding azoxyarene 9 can be generated from reactions of BTZ043 (2) with other nucleophiles.

The problem is worldwide and approximately 10.4 million people become ill and 1.7 million die from TB annually. Treatment of active TB requires committed and diligent use of multidrug therapy over 6-30 months, and success is declining due to the emergence of multidrug resistant (MDR), extensive-drug resistant (XDR), and even totally drug resistant (TDR) strains. While it is unlikely that a single stand-alone drug will be effective against resistant strains of TB, new drugs and combinations with new modes of action are desperately needed.

Addition of $NaBD_4$ to BTZ-043 (2, MW 431; LC/MS M+1, 432) in MeOH or THF/MeOH instantly generated the deep orange solution characteristic of the previously reported Meisenheimer complexes. After 10 min, the reaction was quenched by addition of excess acetic acid relative to the amount of NaBD₄ used. LC/MS analysis of an aliquot of the resulting solution revealed clean formation of a mixture of 6b(D) with a major M+1 peak at m/z=435 (Scheme 3). The solution was then allowed to stir at room temperature exposed to air and was periodically monitored by LC/MS, which indicated slow (24 h), but clean, oxidation of Meisenheimer complexes 6a(D) and 6b(D) to partially deuterated BTZ043, 2D. Extractive workup after 24 h afforded 91% of deuterated BTZ043 (2D). Proton NMR analysis revealed partial deuterium substitution ortho (57% D) and para (24% D) to the nitro group reflecting the differential reactivity at the two positions. A portion of the isolated partially deuterated material was resubjected to the reaction with NaBD₄ to again give a dark orange solution of Meisenheimer complexes. After 5 min, the reaction was quenched with acetic acid and allowed to stir in air. As expected, reoxidation to BTZ043 with enhanced deuterium incorporation was slower. After 3 days, workup gave a 95% recovery of D-BTZ043 (2D). Proton NMR analysis indicated additional deuterium incorporation at the ortho and para positions. Repetition of the reduction/reoxidation process further enhanced the deuterium incorporation but since the reoxidation process in air required several days, alternative reoxidation methods were sought.

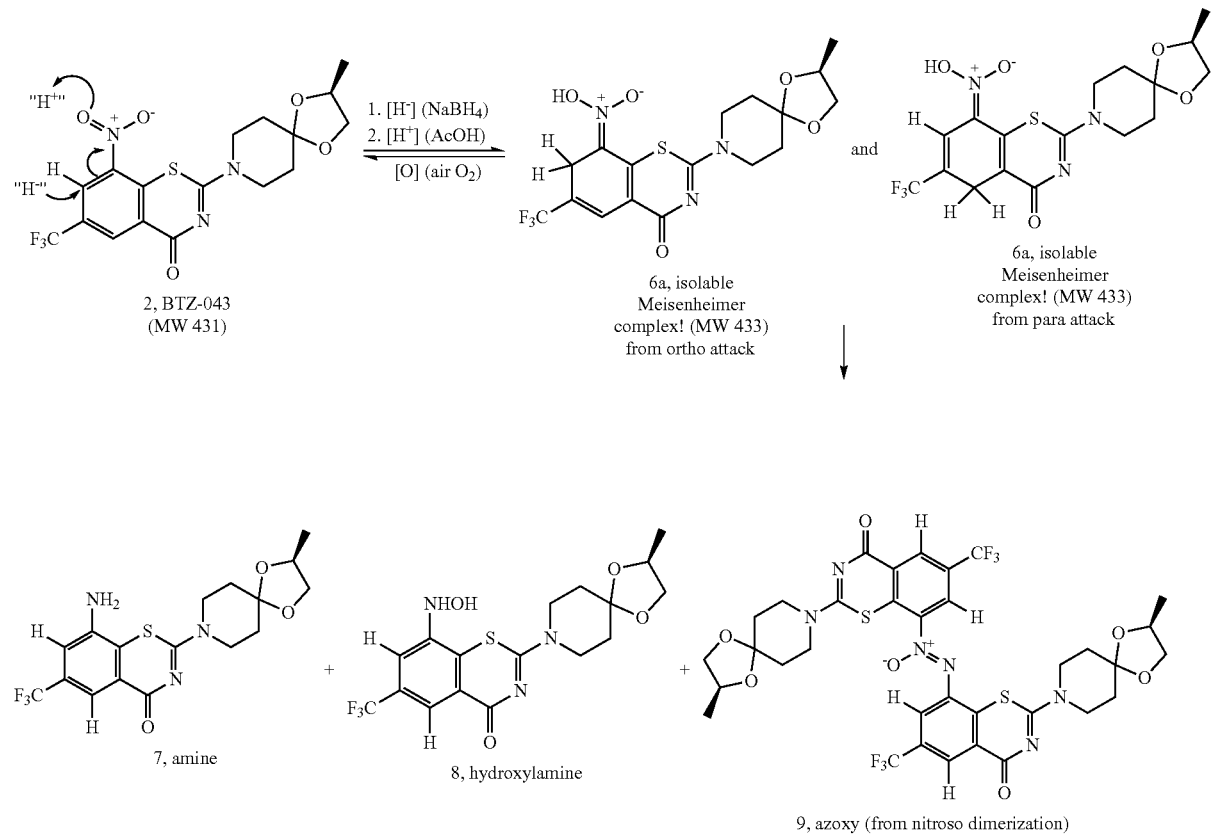

Scheme 2. Hydride-induced Formation of Meisenheimer Complexes and Subsequent Reactions.

Treatment of the mixture of Meisenheimer complexes (6a+6b) with hydrogen peroxide resulted in decomposition. Interestingly, treatment of 6a+6b with oxone generated the corresponding phenol (10, Scheme 4) rather than reforming the aromatic nitro compound (2). However, reaction of 2 (BTZ043) with NaBD₄ as before but with subsequent addition of diisopropylazodicarboxylate (DIAD) induced immediate loss of the orange color characteristic of the mixture of Meisenheimer complexes. LC/MS and HNMR analyses revealed formation of partially deuterated BTZ (2D) (Scheme 4). Thus, rather than waiting days at room temperature for the slow reoxidation process, the reoxidation could be completed quickly. In fact, it was possible to repeat the reduction/oxidation sequence 10 times within a single day to give 2D (D-BTZ043) in a 45% overall yield and enhanced deuterium incorporation (94% ortho and 83% para) for the 10-fold process.

Scheme 3. Reduction of BTZ043 with NaBHD4 Incorporates Deuterium into the BTZ Core.

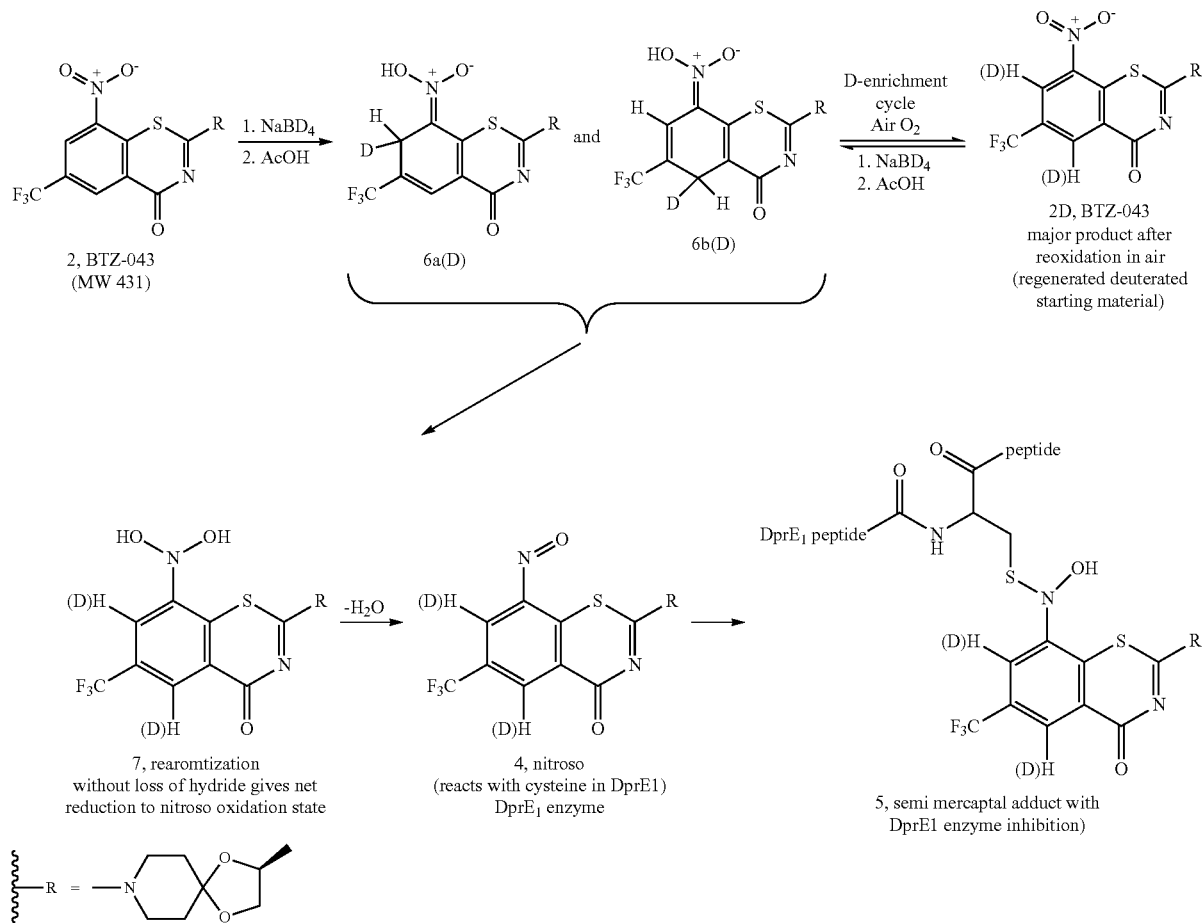

In order to probe the isotope effect on the reoxidation of BTZ043, varying isotopomers of the Meisenheimer complexes 6 were generated and the kinetics of their decomposition studied by UV-visible spectroscopy. The protio compound 6-H$_2$ was generated in methanol by reduction of 2 with NaBH$_4$, followed by quenching with acetic acid, and then allowed to react at 36° C. while its optical spectrum was monitored. A compound with one deuterium and one protium at the sp$^3$-hybridized carbon, 6-HD, was generated by analogous reduction of 2D with NaBH$_4$, while compounds with two deuterium atoms at the sp$^3$-hybridized carbon, 6-D$_2$, were prepared from 2D and NaBD$_4$. In all cases, reactions were carried out under air, though control experiments showed that reactions were only about 30% faster under air than under argon at this temperature.

Scheme 4. Alternative Reoxidation of Meisenheimer Complexes.

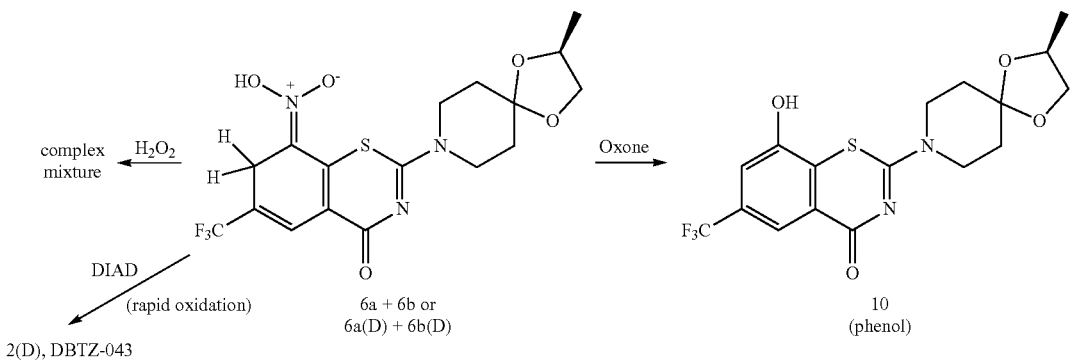

Reactions in all cases displayed clean first-order kinetics with no sign of biphasic behavior (FIG. 1). This suggests that rate differences between 6a and 6b under these conditions are not large. As expected, increasing deuteration leads to significantly decreased rates of reaction, with the kinetic isotope effect (KIE) on monodeuteration $k_{HH}/k_{HD}=2.00\pm0.15$ and the KIE on dideuteration $k_{HH}/k_{DD}=4.7\pm0.3$. The magnitude of the latter KIE indicates the presence of a primary isotope effect, confirming that the C—H bond to the $sp^3$-hybridized carbon in 6 is broken in the rate-determining step of rearomatization. However, the monodeutero compound reacts appreciably more slowly than expected if only a primary isotope effect were present (as an isotope effect $k_{HH}/k_{HD}$ can only be as high as 2.00 if the primary isotope effect were so large that essentially only the C—H bond, not the C-D bond, were ever broken on reaction of 6). This suggests that there must be a significant normal secondary isotope effect in the reaction, and indeed normal secondary isotope effects are often observed in reactions where the reactive carbon is rehybridized from $sp^3$ to $sp^2$ in the transition state of the rate-determining step.

The experimental data are consistent with a primary KIE of $3.2\pm0.6$ and a secondary KIE of $1.46\pm0.26$ in the rearomatization reaction. While primary KIEs have garnered the majority of attention in modulating drug properties, the existence of a significant secondary KIE is of potential interest as well, particularly for a drug like BTZ043, where protium is introduced in vivo in a critical reactive position, so the effect of deuteration may well be carried to a significant extent by its secondary, rather than primary, isotope effect. In this case, for example, the 2-fold longer lifetime of 6-HD compared to 6-$H_2$ is 69% due to the primary KIE, but 31% of the increase in lifetime is due to the secondary KIE.

Both original BTZ043 (2) and the final deuterium enriched sample (2D) were tested for antituberculosis activity and, as expected, had identical potent activity in whole cell assays (<0.004 µM each in MABA media and 0.02-0.03 µM in GAS media using $H_{37}RV$ cells).

In conclusion, reduction of the potent anti-TB agent, BTZ043, with deuteride followed by reoxidation incorporates deuterium into the nitroaromatic warhead. The deuterated products are rapidly reduced by hydride to form Meisenheimer complexes that more slowly regenerate the deuterated aromatic core/warhead.

Scheme 5. Tested Reaction Conditions.

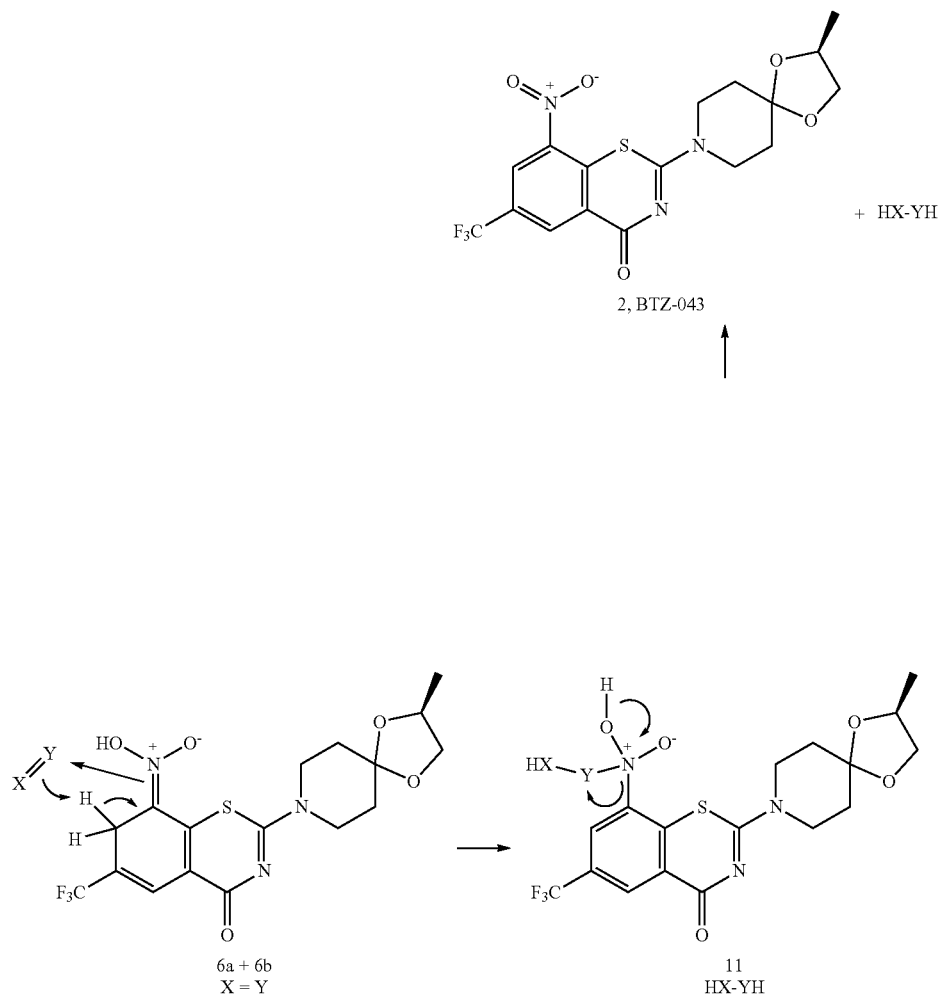

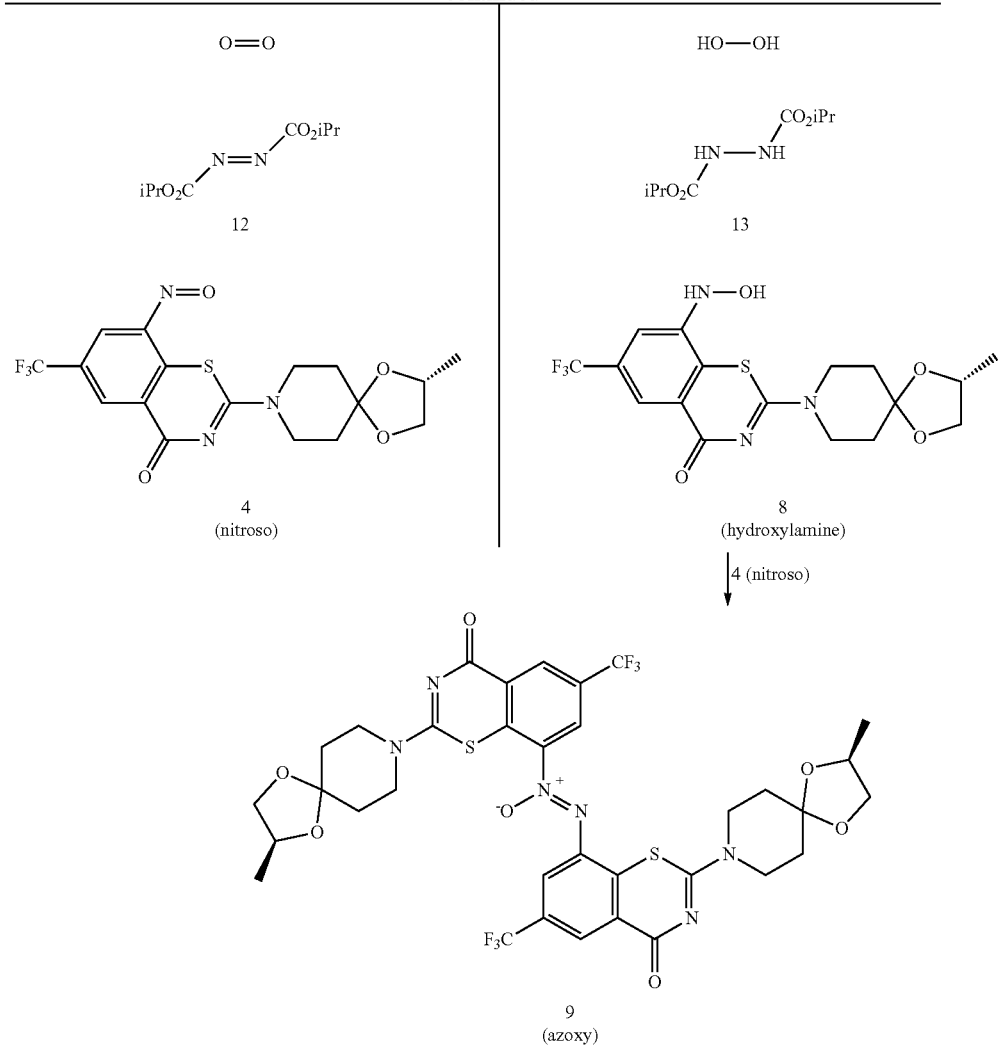

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, fumarate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet.

Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antimicrobial agents and have higher potency and/or reduced toxicity as compared to a non-deuterated antimicrobial agent.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like.

The ability of a compound of the invention to treat infections may be determined by using assays well known to the art. For example, the design of treatment protocols, toxicity evaluation, data analysis, quantification of bacterial cell-kill.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthesis

General Methods. All solvents and reagents were obtained from commercial sources and used without further purification. Thin layer chromatography (TLC) was performed with Al-backed Merck 60-F254 silica gel plates using a 254 nm lamp for visualization. HPLC-MS mass measurements were used to determine reaction progress and compound purity, as well as structural consistency. The HPLC-MS studies were performed with Bruker MicroTOF-QII, quadrupole time-of-flight mass spectrometer coupled via electrospray ionization with a Dionex Ultimate 3000 RSLC system. A 15 min binary gradient separation on a Dionex Acclaim™ RSLC 120 C18 column (2.2 µm, 120 Å, 2.1 mm id×100 mm) kept at 40° C. with a flow rate of 0.4 mL/min was run under the following conditions: solvent A=water with 0.1% formic acid, solvent B=acetonitrile with 0.1% formic acid, A:B=90:10 for 1 min followed by a 10 min linear ramp to A:B 5:95 and keep the ratio for 2 minutes before returning to initial conditions for 2 min.

Deuterated BTZ043, 2D

Method A (reduction followed by air oxidation). BTZ043 (2, 431 mg, 1 mmol) was dissolved in 5 mL of THF in a 100 mL round bottomed flask by stirring at room temperature. Then 25 mL of MeOH was added to give a clear light-yellow solution. Solid $NaBD_4$ (205 mg, 5 mmol) was added portionwise over a few minutes with stirring. The reaction instantly turned red orange, indicative of formation of Meisenheimer complexes 6a(D) and 6b(D) (J. Am. Chem. Soc. 2013, 135, 3539; J. Org. Chem. 1963, 28, 1430). TLC and LC/MS indicated complete absence of starting material and clean conversion to the Meisenheimer complexes.

The excess $NaBD_4$ was quenched by addition of 425 µL of HOAc and the solution was allowed to stir at room temperature. The orange/red color of the solution slowly changed back to light yellow and after 24 h analysis of the reaction solution by TLC and LC/MS revealed regeneration of the nitro aromatic core of BTZ (2D) and a trace amount of the corresponding partially deuterated aniline, 8D. The solution was concentrated to ~10 mL, 25 mL of $CH_2Cl_2$ was added and the resulting organic solution was sequentially extracted with 15 mL of $H_2O$, 15 mL of 10% citric acid, 15 mL of $H_2O$, 15 mL of satd. $NaHCO_3$, 15 mL of $H_2O$ and, finally, 15 mL of brine. The organic layer was then dried over $MgSO_4$, filtered and evaporated to give 394 mg (91.4%) of deuterated BTZ043, 2D. The 1H NMR spectrum of 2D was identical to that of starting BTZ043 (2) except that integration indicated partial deuterium substitution ortho (75% D) and para (45% D). The product was resubjected to the reaction conditions to enhance deuterium enrichment. The air induced re-oxidation required 3 d. After the same workup, 1H NMR analysis indicated enhanced, but not complete deuterium incorporation (90% ortho D, 69% para D).

Method B (reduction followed by oxidation with diisopropyl azodicarboxylate). BTZ043 (2, 0.05 mmol, 22 mg) was dissolved in 1 mL of THF and diluted with 5 mL of MeOH to give a clear solution. To a scintillation vial fitted with a stir bar was added $NaBD_4$ (10 mg, 0.25 mmol). Then the BTZ THF/MeOH solution was added to the scintillation vial to give an orange solution. The solution was monitored by TLC as well as LC/MS and showed that the BTZ was totally converted to the regioisomeric mixture of Meisenheimer complexes. Then, to this orange solution was added DIAD (diisopropyl azodicarboxylate, 0.05 mmol, 10 µL). As soon as DIAD was added, the orange color disappeared. Then TLC as well as LC/MS indicated that the reduction products had re-oxidized to give partially deuterated BTZ as the major product.

To this reaction mixture was added $NaBD_4$ (10 mg, 0.25 mmol) again to again reduce the partially deuterated BTZ043. Then DIAD (0.05 mmol, 10 µL) was added again to regenerate the BTZ043 with enhanced deuteration. The reduction and the re-oxidation sequence was repeated 10 times. The reaction was quenched by addition of AcOH and then concentrated under reduced pressure. The residue was purified by silica gel column chromatography eluting with hexanes/EtOAc to give deuterated BTZ043 (2D), as a yellow solid in 45.5% overall yield for the 10-step process.

Kinetic Studies

BTZ043 (2) or deuterated BTZ043 (2D) (4.3 mg, 0.01 mmol) was dissolved in 2 mL of THF in a 10 mL volumetric flask and diluted to 10 mL with MeOH to give stock solution 1. A portion (1 mL) of stock solution 1 was transferred to another 10 mL volumetric flask and diluted to 10 mL with MeOH to give stock solution 2. To a scintillation vial fitted with a stir bar was added 10 mL of stock solution 2. The solution was stirred and 20 mg of $NaBH_4$ (or $NaBD_4$) was added to give a dark orange color. TLC indicated no remaining BTZ043 or deuterated BTZ043. The reaction was quenched by addition of 200 µL of AcOH. The mixture was stirred in air and 2 mL of the solution was transferred to each of three UV/Vis cuvettes. The cuvettes were placed in a cell holder maintained at 36° C. using a recirculating bath and the optical spectra measured over time on a ThermoFisher Evolution Array spectrophotometer. Data were analyzed by fitting the absorbance at 450 nm to a single-exponential decay using the program KaleidaGraph (Synergy Software, version 4.1.3).

Example 2. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | >500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:
1. A method for forming a deuterated compound of Formula IA, IB, or IC:

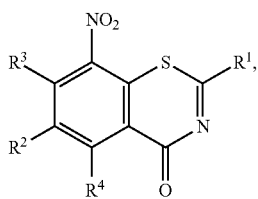
(IA)

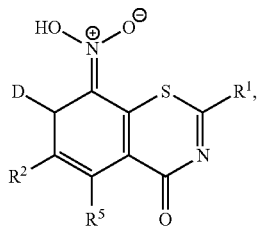
(IB)

or

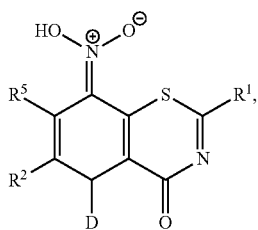
(IC)

or an azoxy dimer or salt thereof;
wherein
R¹ is 2-(C₁-C₆)alkyl-1,4-dioxa-8-azaspiro[4.5]decan-8-yl or 4-((C₃-C₆)cycloalkyl methyl)piperazin-1-yl;
R² is halo, cyano, —(C₁-C₃)alkyl, or —O(C₁-C₃)alkyl, wherein —(C₁-C₃)alkyl or —O(C₁-C₃)alkyl has 2 to 7 halo substituents;
R³ and R⁴ are independently H, D, halo, hydroxyl, cyano, —(C₁-C₆)alkyl; and
R⁵ is H, D, halo, hydroxyl, cyano, —(C₁-C₆)alkyl;
comprising:
a) reacting a deuteride reducing agent and a compound of Formula IA wherein R³ and R⁴ are H to form a reduced intermediate; and
b) reacting the reduced intermediate and an oxidizing agent to form a compound of Formula IA wherein at least one of R³ or R⁴ is D; or
c) reacting the reduced intermediate and a protic reagent to form a compound of Formula IB or IC;
wherein the deuterated compound of Formula IA, IB, or IC is thereby formed.

2. The method of claim 1 further comprising repeating steps a) and b) to increase deuterium incorporation in a compound of Formula IA; or
repeating steps a) and c) to increase deuterium incorporation in a compound of Formula IB or IC.

3. The method of claim 1 wherein the reducing agent is a metal borodeuteride.

4. The method of claim 1 wherein the oxidizing agent is a diialkylazodicarboxylate.

5. The method of claim 1 wherein the protic reagent is an organic acid.

6. The method of claim 1 wherein R¹ is 2-methyl-1,4-dioxa-8-azaspiro[4.5]decan-8-yl and R² is CF₃; or R¹ is 4-(cyclohexylmethyl)piperazin-1-yl.

7. The method of claim 1 wherein R² is CF₃.

8. A method for treating a microbial infection comprising administering to a subject in need thereof a therapeutically effective amount of a compound of Formula IA, IB, or IC:

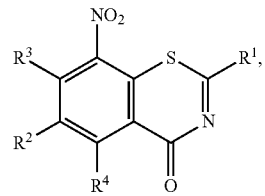
(IA)

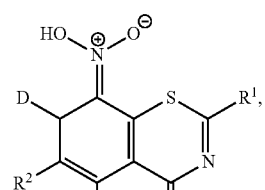
(IB)

or

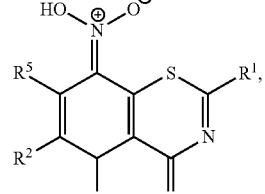
(IC)

or an azoxy dimer or pharmaceutically acceptable salt thereof;
wherein
R¹ is 2-(C₁-C₆)alkyl-1,4-dioxa-8-azaspiro[4.5]decan-8-yl or 4-((C₃-C₆)cycloalkyl methyl)piperazin-1-yl;
R² is halo, cyano, —(C₁-C₃)alkyl, or —O(C₁-C₃)alkyl, wherein —(C₁-C₃)alkyl or —O(C₁-C₃)alkyl has 2 to 7 halo substituents;
R³ and R⁴ are independently H, D, halo, hydroxyl, cyano, —(C₁-C₆)alkyl, wherein at least one of R³ or R⁴ is D; and
R⁵ is H, D, halo, hydroxyl, cyano, —(C₁-C₆)alkyl;
thereby killing or inhibiting the growth of at least a portion of a plurality of microorganisms in the subject.

9. The method of claim 8 wherein R¹ is 2-methyl-1,4-dioxa-8-azaspiro[4.5]decan-8-yl; or R¹ is 4-(cyclohexylmethyl)piperazin-1-yl.

10. The method of claim 8 wherein R² is CF₃, R³ is D, and R⁴ is H.

11. The method of claim 8 wherein R² is CF₃, R³ is H, and R⁴ is D.

12. The method of claim 8 wherein R² is CF₃, and R³ and R⁴ are D.

13. The method of claim 8 wherein R² is CF₃ and R⁵ is H or D.

14. The method of claim 8 wherein the compound is:
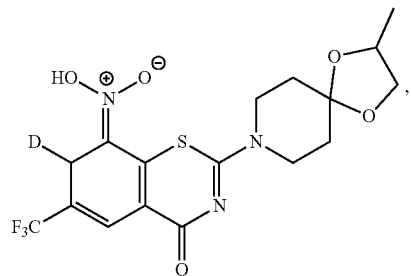
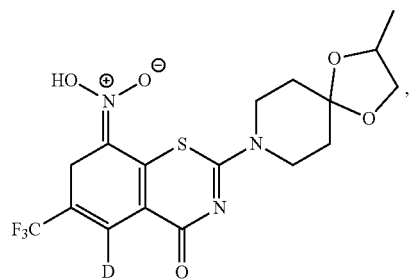
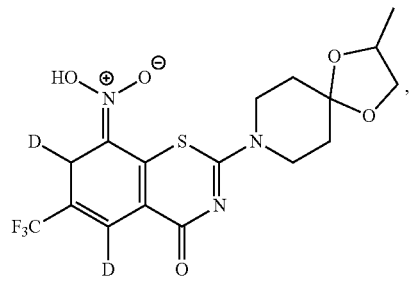
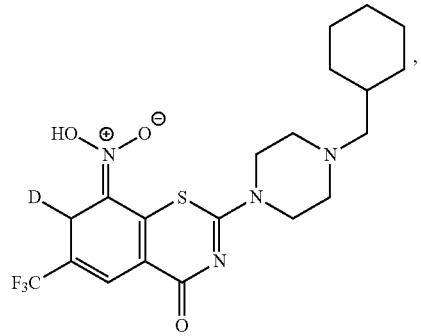
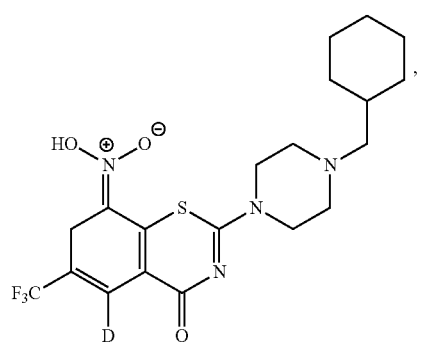
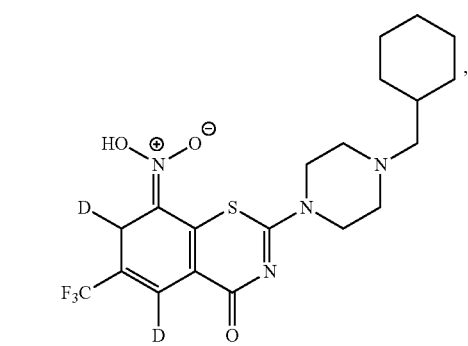
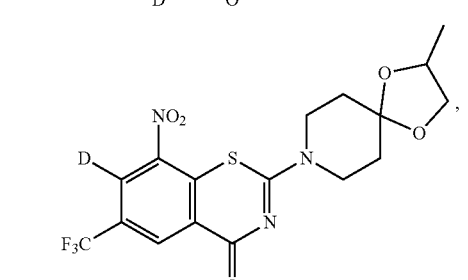
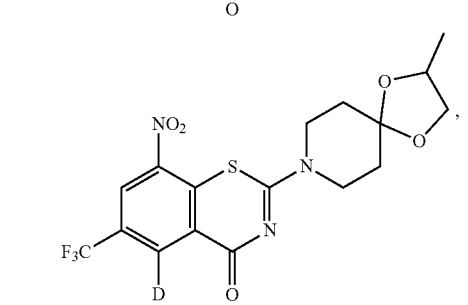
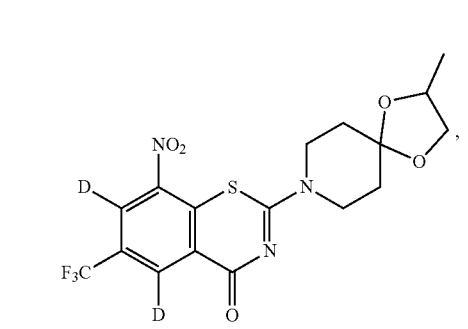
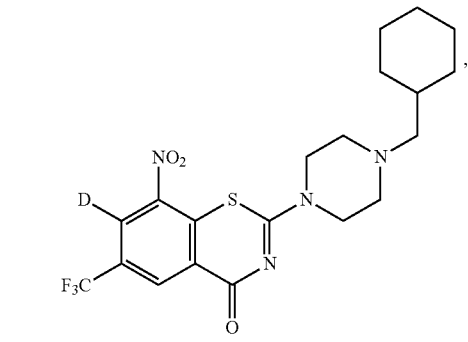

-continued

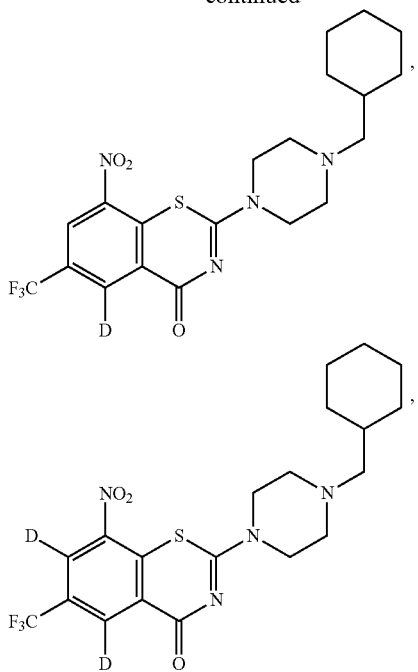

or the azoxy dimer thereof.

15. The method of claim 8 wherein the microbial infection is a mycobacterial infection.

16. The method of claim 15 wherein the mycobacterial infection is tuberculosis or leprosy.

17. A compound of Formula IA, IB, or IC:

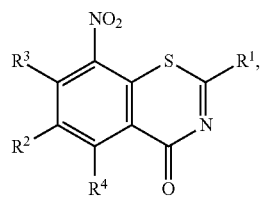
(IA)

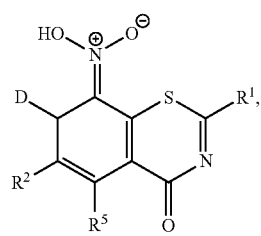
(IB)

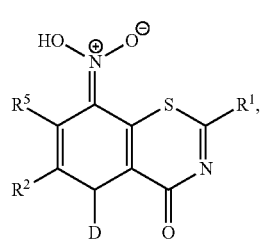
(IC)

or an azoxy dimer or salt thereof;
wherein
$R^1$ is 2-($C_1$-$C_6$)alkyl-1,4-dioxa-8-azaspiro[4.5]decan-8-yl or 4-((($C_3$-$C_6$)cycloalkyl methyl)piperazin-1-yl;
$R^2$ is halo, cyano, —($C_1$-$C_3$)alkyl, or —O($C_1$-$C_3$)alkyl, wherein —($C_1$-$C_3$)alkyl or —O($C_1$-$C_3$)alkyl has 2 to 7 halo substituents;
$R^3$ and $R^4$ are independently H, D, halo, hydroxyl, cyano, —($C_1$-$C_6$)alkyl, wherein at least one of $R^3$ or $R^4$ is D; and
$R^5$ is H, D, halo, hydroxyl, cyano, —($C_1$-$C_6$)alkyl.

18. The compound of claim 17 wherein $R^1$ is 2-methyl-1,4-dioxa-8-azaspiro[4.5]decan-8-yl; or $R^1$ is 4-(cyclohexylmethyl)piperazin-1-yl.

19. The compound of claim 17 wherein $R^2$ is $CF_3$, $R^3$ is D, and $R^4$ is H; or
$R^2$ is $CF_3$, $R^3$ is H, and $R^4$ is D; or
$R^2$ is $CF_3$, and $R^3$ and $R^4$ are D; or
$R^2$ is $CF_3$ and $R^5$ is H or D.

20. The compound of claim 17 wherein the compound is:

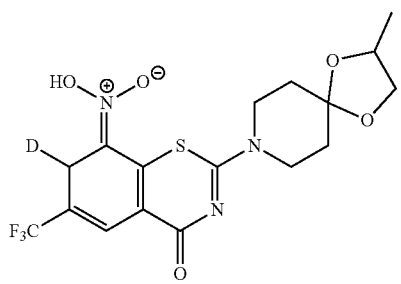

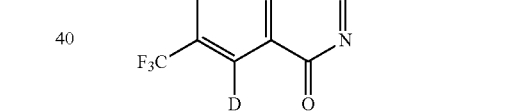

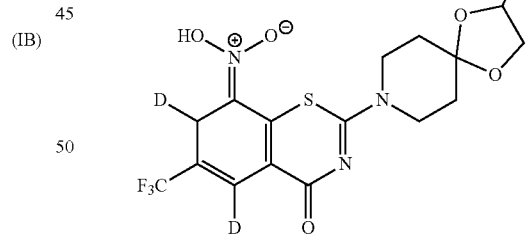

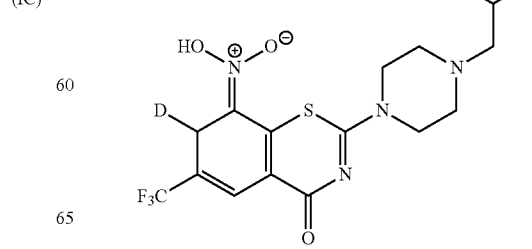

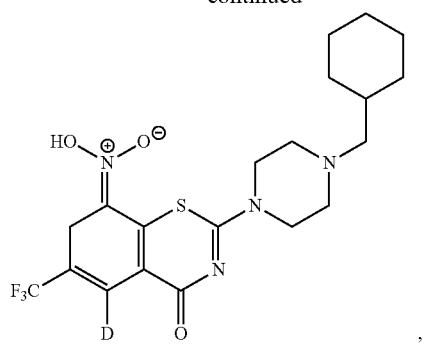
,
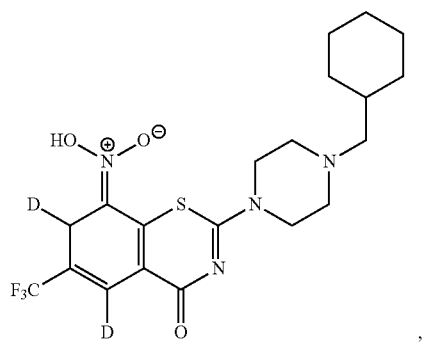
,
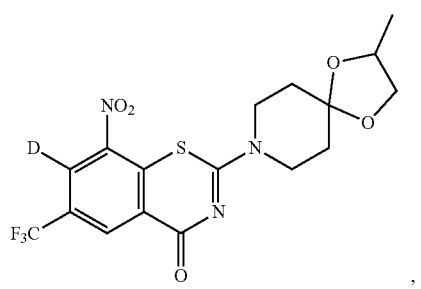
,
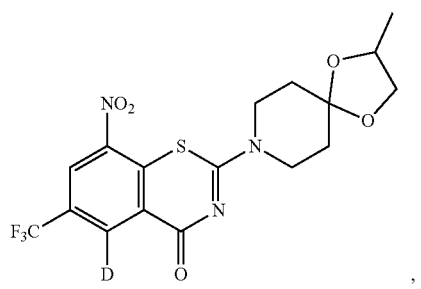
,
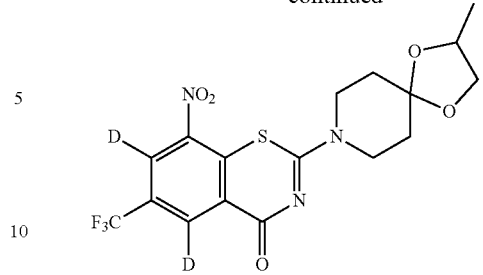
,
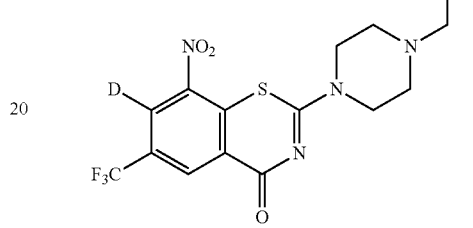
,
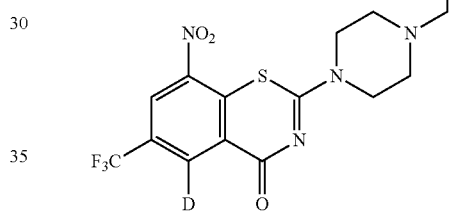
,
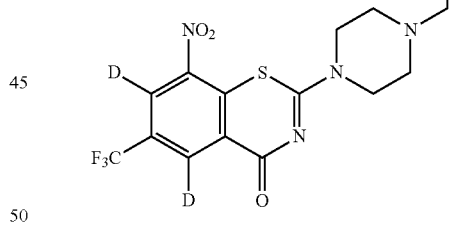
,
or the azoxy dimer thereof.
* * * * *